US011291392B2

(12) United States Patent
Olivier (10) Patent No.: US 11,291,392 B2
(45) Date of Patent: Apr. 5, 2022

(54) REAL-TIME AND CONTINUOUS DETERMINATION OF EXCESS POST-EXERCISE OXYGEN CONSUMPTION AND THE ESTIMATION OF BLOOD LACTATE

(71) Applicant: LifeQ Global Limited, Dublin (IE)

(72) Inventor: Laurence Richard Olivier, Alpharetta, GA (US)

(73) Assignee: LifeQ Limited Limited, Dublin (IE)

( * ) Notice: Subject to any disclaimer, the term of this patent is extended or adjusted under 35 U.S.C. 154(b) by 436 days.

(21) Appl. No.: 15/123,082

(22) PCT Filed: Mar. 2, 2015

(86) PCT No.: PCT/US2015/018303
§ 371 (c)(1),
(2) Date: Sep. 1, 2016

(87) PCT Pub. No.: WO2015/134382
PCT Pub. Date: Sep. 11, 2015

(65) Prior Publication Data
US 2017/0105664 A1    Apr. 20, 2017

Related U.S. Application Data

(60) Provisional application No. 61/947,096, filed on Mar. 3, 2014.

(51) Int. Cl.
*A61B 5/1455*    (2006.01)
*A61B 5/024*    (2006.01)
(Continued)

(52) U.S. Cl.
CPC ...... *A61B 5/14551* (2013.01); *A61B 5/02416* (2013.01); *A61B 5/02438* (2013.01);
(Continued)

(58) Field of Classification Search
CPC ... A61B 5/14551; A61B 5/4866; A61B 5/222; A61B 5/7278; A61B 5/02438; A61B 5/14546; A61B 5/02416
See application file for complete search history.

(56) References Cited

U.S. PATENT DOCUMENTS 7,805,186 B2   9/2010   Pulkkinen
8,465,397 B2   6/2013   Saalasti et al.
(Continued)

FOREIGN PATENT DOCUMENTS

CN   109330583   *   2/2019   ........... A61B 5/0245
TW         555544       10/2003
(Continued)

OTHER PUBLICATIONS

CN 109330583 Abstract only.*
(Continued)

*Primary Examiner* — Jacqueline Cheng
*Assistant Examiner* — Tho Q Tran
(74) *Attorney, Agent, or Firm* — Smith Gambrell & Russell LLP (57) ABSTRACT

The current invention pertains to an apparatus and method for the determination of excess post-exercise oxygen consumption (EPOC) and the estimation of blood lactate levels. While these exercise parameters are traditionally determined using indirect calorimetry and blood sampling, this invention provides a method for the determination of these parameters using heart rate data. A wearable photoplethysmography device for measuring heart rate is included as an exemplary embodiment, however, the method of the current inventions can also be used with heart rate data from any heart rate monitor. In an embodiment of the present invention a supply demand differential equation is used to continuously monitor EPOC in real-time. Furthermore, blood (Continued)

lactate levels can also be estimated as a function of EPOC. Importantly, the process of determining EPOC and blood lactate can be linked to a biomathematical model of human physiology to access additional parameters such as hormonal changes, body composition changes or other physiological fluctuations or transient physiological behavior.

18 Claims, 4 Drawing Sheets

(51) Int. Cl.
 *A61B 5/00* (2006.01)
 *A61B 5/145* (2006.01)
 *A61B 5/22* (2006.01)

(52) U.S. Cl.
 CPC .......... *A61B 5/14546* (2013.01); *A61B 5/222* (2013.01); *A61B 5/4866* (2013.01); *A61B 5/7278* (2013.01)

(56) References Cited

U.S. PATENT DOCUMENTS

| | | | |
|---|---|---|---|
| 2001/0020135 A1 | 9/2001 | Heikkila | |
| 2001/0027266 A1 | 10/2001 | Hautala et al. | |
| 2006/0004265 A1* | 1/2006 | Pulkkinen | A61B 5/0205 600/300 |
| 2007/0049462 A1* | 3/2007 | Asukai | A63B 71/06 482/8 |
| 2007/0249949 A1 | 10/2007 | Hadley | |
| 2009/0069156 A1 | 3/2009 | Kurunmaeki et al. | |
| 2011/0040193 A1 | 2/2011 | Seppanen et al. | |
| 2011/0263993 A1 | 10/2011 | Martikka et al. | |
| 2012/0010488 A1 | 1/2012 | Henry et al. | |
| 2012/0077873 A1 | 3/2012 | Zachwieja et al. | |
| 2012/0283525 A1 | 11/2012 | Kuroda | |
| 2014/0128691 A1* | 5/2014 | Olivier | A61B 5/0833 600/301 |
| 2016/0184637 A1* | 6/2016 | Pulkkinen | G16H 20/30 600/301 |

FOREIGN PATENT DOCUMENTS

| | | |
|---|---|---|
| WO | WO 2013/009589 | 1/2013 |
| WO | WO2013009589 | 1/2013 |
| WO | WO 2013/056154 | 4/2013 |

OTHER PUBLICATIONS

Lemay et al., Application of Optical Heart Rate Monitoring, Wearable Sensors, Ch. 2.3, pp. 105-129, 2014. (Year: 2014).*

Ahtinen et al., Using heart rate monitors for personal wellness—the user experience perspective, Conf. Proc. IEEE Eng. Med. Biol. Soc. (2008) (Year: 2008).*

Firstbeat Technologies, Inc., "Indirect EPOC Prediction Method Based on Heart Rate Measurement," Feb. 2007, retrieved from the internet on Sep. 9, 2017 atwww.sporttest.nl/wp-content/uploads/2013/05/Indirecte-EPOC-voorspelling-gebasseerd-op-hartslag.pdf; 5 pages.

The supplementary European Search Report issued by the European Patent Office on Oct. 11, 2017 for corresponding European Patent Application No. 15759071.2; 10 pages.

The Office Action released by the Taiwan Patent Office released in corresponding Taiwan Patent Application No. 104106746 dated May 31, 2019; 8 pages.

The Communication Pursuant to Article 94(3) released by the European Patent Office released in corresponding European Patent Application No. 15759071.2 dated Jun. 4, 2021; 4 pages.

* cited by examiner

REAL-TIME AND CONTINUOUS DETERMINATION OF EXCESS POST-EXERCISE OXYGEN CONSUMPTION AND THE ESTIMATION OF BLOOD LACTATE

FIELD OF THE INVENTION

The present invention pertains to the field of exercise science and physiological parameter determination. Specifically, the current invention relates to the determination of excess post-exercise oxygen consumption (EPOC), informally referred to as afterburn, as well as the estimation of blood lactate levels. The apparatus and method of the invention relies primarily on heart rate data gathered by a wearable photoplethysmography (PPG) device and/or any other heart rate monitor. Disclosed is a unique method for determining EPOC and subsequently estimated blood lactate, from a PPG signal, using a supply-demand differential equation and without the need for expensive, uncomfortable and/or invasive procedures such as indirect calorimetry and blood sampling.

BACKGROUND OF THE INVENTION

In the exercise and physical fitness sphere, the ability to track and assess excess post-exercise oxygen consumption (EPOC) and blood lactate levels provides an individual and his/her trainer with important information about cardiorespiratory fitness, how hard the individual has been training and how a training or recovery program can be optimized to suit the individual. EPOC is defined as the measurable increase in the rate of oxygen uptake following exercise, especially after exercise that is at or above ~50-60% of the individual's maximal oxygen consumption ($VO_{2\ max}$). Exercise causes a marked disruption in the body's homeostasis and therefore an increase in oxygen consumption post-exercise is required to restore the body to its resting state. The amount of EPOC accumulated during exercise has been shown to be affected by both the intensity and duration of exercise as well as other factors such as type of exercise and physical fitness level. Studies have shown that EPOC has a curvilinear relationship with exercise intensity and a linear relationship with the duration of exercise. In addition, trained individuals typically have a faster EPOC recovery time than untrained individuals.

Since the discovery of EPOC in 1910, the rationale behind why an increase in oxygen consumption post-exercise is observed has evolved with the publication of new evidence. It is now generally accepted that the increase in oxygen consumption following exercise is needed in order to fulfill a number of different roles which include: the replenishment of phosphagen stores that have become depleted, replenishment of oxygen stores (myoglobin and hemoglobin), the removal of lactate (via the conversion to glycogen in the liver or via oxidation to pyruvate in the kidneys, heart and liver so that it can enter the Kreb cycle and produce ATP), restoration of muscle glycogen stores, the fueling of an increase in metabolism that occurs with an increase in temperature and circulation, catecholamine release, activation of the sympathetic nervous system, triacylglycerol/fatty acid (TCA/FA) cycling, the shift from carbohydrate to fat substrate utilization and restorative processes such as reparation of cells. The EPOC period is classically divided into a, fast component, which decays exponentially and a slow component, which proceeds the fast component and has a linear decay. There are, however, conflicting opinions as to which mechanisms are responsible for driving each of these components.

During strenuous exercise, when the body can no longer keep up with the current level of exercise intensity by means of its aerobic energy production system, the anaerobic energy system supplies the body with extra energy and in doing so creates lactate as a byproduct. Since the removal of lactate is one of the processes that occurs during the EPOC period, EPOC and blood lactate profiles are related. Blood lactate is a degradation product of glucose, the primary energy source, and the point at which lactate levels start to rise rapidly during exercise is termed the lactate threshold. The lactate threshold is a predictor of exercise performance and is directly related to an individual's $VO_{2\ max}$ score. The lactate threshold of trained individuals will typically occur at 70-80% $VO_{2\ max}$ whereas in untrained individuals it occurs much sooner at around 50-60%. Lactate is present in the bloodstream at rest at about 1-2 mmol/L, however, this can rise to above 20 mmol/L during strenuous exercise.

Several prior art methods exist for the determination of exercise-related parameters such as EPOC and blood lactate. In patent EP 2371278 to Suunto Oy, exercise parameters such as recovery time and energy consumption are calculated from what they term the "changed pulse value". This value is calculated by deducting a recovery pulse from a heart rate measured directly using a physiological sensor. The recovery pulse is defined as the pulse level achieved when exercise is interrupted. This is based on tabulated pre-data which describes the level to which the pulse would increase if the current exercise intensity continues for a long period of time (what they term the saturation level). The recovery pulse is also based on a fitness index which describes the current fitness level of the subject. U.S. Pat. No. 7,192,401 to Firstbeat Technologies discloses a method for estimating a body fatigue index (BFI) which is based on a number of factors including: a measurement of the intensity of the exercise, a pre-determined initial BFI, a calculation of upslope and downslope components, a prediction of the time interval required for recovery as well as measured heart rate data. The BFI is subsequently used in an estimation of oxygen consumption and energy consumption and this process is applied to a wearable computer, PC-software and/or ECG/pulse monitoring equipment. In U.S. Pat. No. 7,805,186 a method and wearable device for the determination of continuous, real-time EPOC is described. EPOC is determined using a measurement of exercise intensity winch may include external power, motion, energy consumption, heart rate, oxygen consumption, respiration rate or heat flow from the surface of the skin. In an embodiment of this invention the heart rate, respiration rate and load stage (oxygen consumption) are all used to determine the percentage share of maximum oxygen consumption, which is subsequently used to determine EPOC. In addition, other parameters which are based on EPOC are output by the device. These include target state, intensity of future exercise and duration of remaining exercise. Training effect is also determined based on the EPOC peak value. Lastly, U.S. Pat. No. 8,292,820 to Suunto Oy describes a wrist-worn sensor that measures a hemodynamic signal and uses this signal with a low pass filter to determine respiration frequency. Respiration frequency is subsequently used to determine EPOC or a derivative thereof.

Prior art describing methods for the estimation of blood lactate levels also exists. EP 1127543 to Polar Electro Oy describes a method which uses a mathematical neural network physiological model that includes parameters such as age, weight, height, gender, stress level, fitness level (in the form of maximal oxygen consumption), lactate production rate, lactate removal rate and blood volume. Heart rate data is then fed into the model, including an estimation of max heart rate (based on age) and the blood lactate concentration is estimated. These models are trained with large datasets and the estimated lactate concentration can also be used as an estimation of the duration of recovery from exercise. Patent application US 20060234386 uses a different approach which uses near-infrared Raman spectroscopy to determine lactate concentration.

The current invention proposes a method for the determination of a real-time continuous projection of EPOC and the subsequent estimation of current blood lactate levels by way of a simple heart rate measurement and a supply demand differential equation that is unique to this invention. The formulations (i) describe EPOC accumulation and decay in a, mechanistic fashion and (ii) can be used to continuously and instantaneously determine EPOC. The heart rate measurements which are used to determine EPOC can be taken using the apparatus of the current invention, a wearable PPG device, or from any other heart rate monitor. Continuous access to EPOC levels and a blood lactate profile during and after exercise will provide valuable information pertaining to the physiological effect of exercise to motivate and/or guide users to achieve and maintain personal health, wellness and fitness goals.

SUMMARY OF THE INVENTION

The present invention overcomes problems and obstacles associated with the traditional measurement of EPOC and blood lactate by disclosing a method for continuous and real-time determination of these parameters in a setting that is accessible to all individuals. The apparatus is comprised of a wearable PPG device which houses an optical sensor(s) and acquires absorbance data when in contact with the user's skin. Heart rate is then determined from the PPG absorbance data on the processor of the device or by other means. The heart rate data, measured from the wearable or from any heart rate monitor, is then used by the current method to track and monitor EPOC and estimated blood lactate over time. In an embodiment of the present invention the exercise intensity or Percentage $VO_{2max}$ of a subject is used in a supply-demand differential equation to continuously project EPOC at any given time. This invention also describes how estimated blood lactate can be calculated as a function of EPOC.

The invention accordingly comprises several steps which are reliant on the relationship between the $HR_{reserve}(HR_{max}-HR_{rest})$ and $VO_{2reserve}$ ($VO_{2max}-VO_{2rest}$). Once this is established, Percentage $VO_{2max}$ can be calculated and included in a differential equation that determines the change in EPOC, as a function of Percentage $VO_{2max}$ and also takes into account the EPOC from the previous time point, since there is an accumulation of EPOC over time. With this knowledge, blood lactate can be estimated as a function of EPOC. Included in this equation are values for $lactate_{max}$, dvar (a parameter that ensures that lactate does not drop below 0 mmol/l during rest) and klactate, an empirically derived variable. The practical usage of the differential equation to determine EPOC and the equation for blood lactate estimation are discussed in the detailed description. This method for EPOC and blood lactate determination can also be linked directly to a cloud-based biomathematical model of metabolism, body composition change, hormonal changes or any other biomathematical model that describes a physiological process so as to access additional parameters. While the present invention is described in detail with reference to various descriptions in subsequent pages, it will be appreciated that the present invention is not limited to the description herein, and that modifications may be made without departing from the scope of the invention defined in the accompanying description.

BRIEF DESCRIPTION OF THE DRAWINGS

The preferred embodiments of the invention will be described by way of example only, with reference to the accompanying drawings.

DETAILED DESCRIPTION OF THE PREFERRED EMBODIMENTS

The following detailed description and drawings describe different aspects of the current invention. The description and drawings serve to enable one skilled in the art to fully understand the current invention and are not intended to limit the scope of the invention in any manner. Before the present methods and systems are disclosed and described, it is to be understood that the methods and systems are not limited to special methods, special components, or to particular implementations. It is also to be understood that the terminology used herein is for the purpose of describing particular aspects only and is not intended to be limiting. As used in the specification and the appended claims, the word "comprise" and variations of the word, such as "comprising" and "comprises," means "including but not limited to," and is not intended to exclude, for example, other components or steps. "Exemplary" means "an example of" and is not intended to convey an indication of a preferred or ideal embodiment. "Such as" is not used in a restrictive sense, but for explanatory purposes. The singular forms "a," "an," and "the" also include plural elements unless the context clearly dictates otherwise. "Optional" or "optionally" means that the subsequently described event or circumstance may or may not occur and that the description includes instances where said event or circumstance occurs and instances where it does not.

Figure 1:
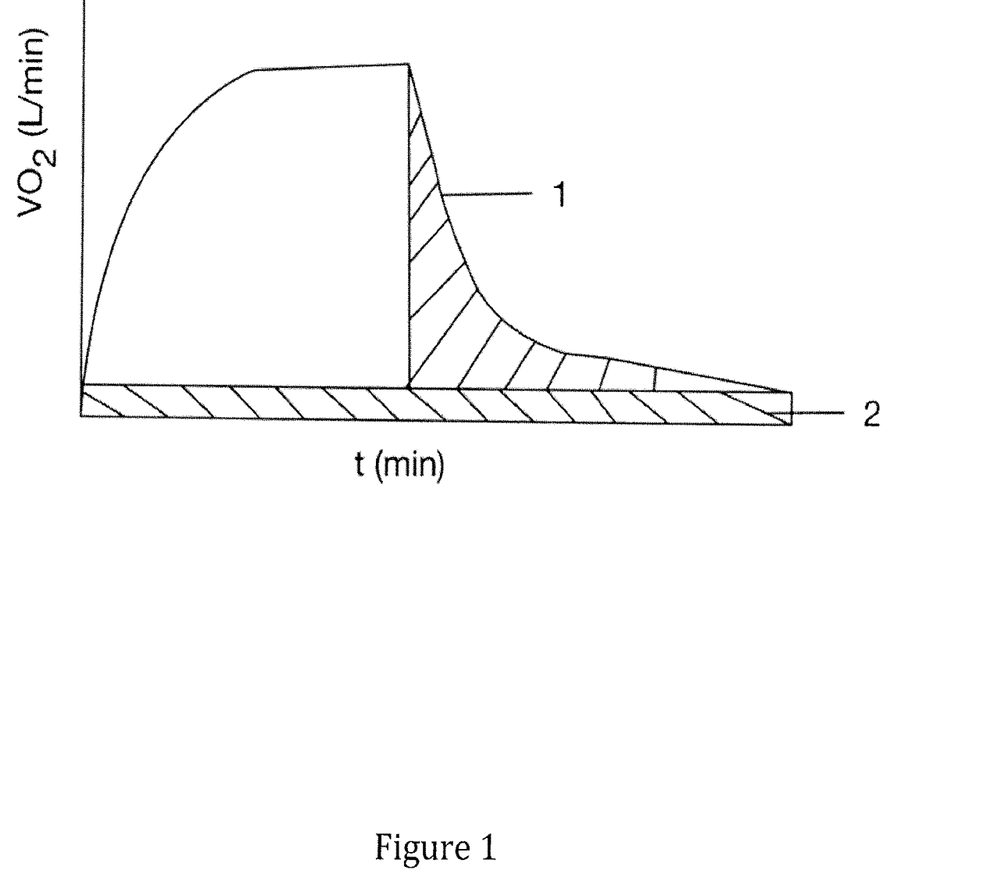
FIG. 1: Time plot of excess post-exercise oxygen consumption after exercise.

FIG. 1 depicts a time plot of oxygen consumption during and after a bout of strenuous exercise. Since EPOC is defined as a measurable increase in oxygen consumption following exercise, it is calculated by integrating the area underneath the curve after exercise (1) and subtracting the resting oxygen consumption (2) from this value. This method relies on the direct measurement of oxygen consumption and is the gold standard for measuring EPOC. The method of the current invention aims to circumvent this problem by providing a means for determining continuous, real-time EPOC as well as estimated blood lactate from heart rate data. The wearable PPG device of the current invention provides a means for collecting the heart rate data that is necessary to determine these exercise parameters.

Figure 2:
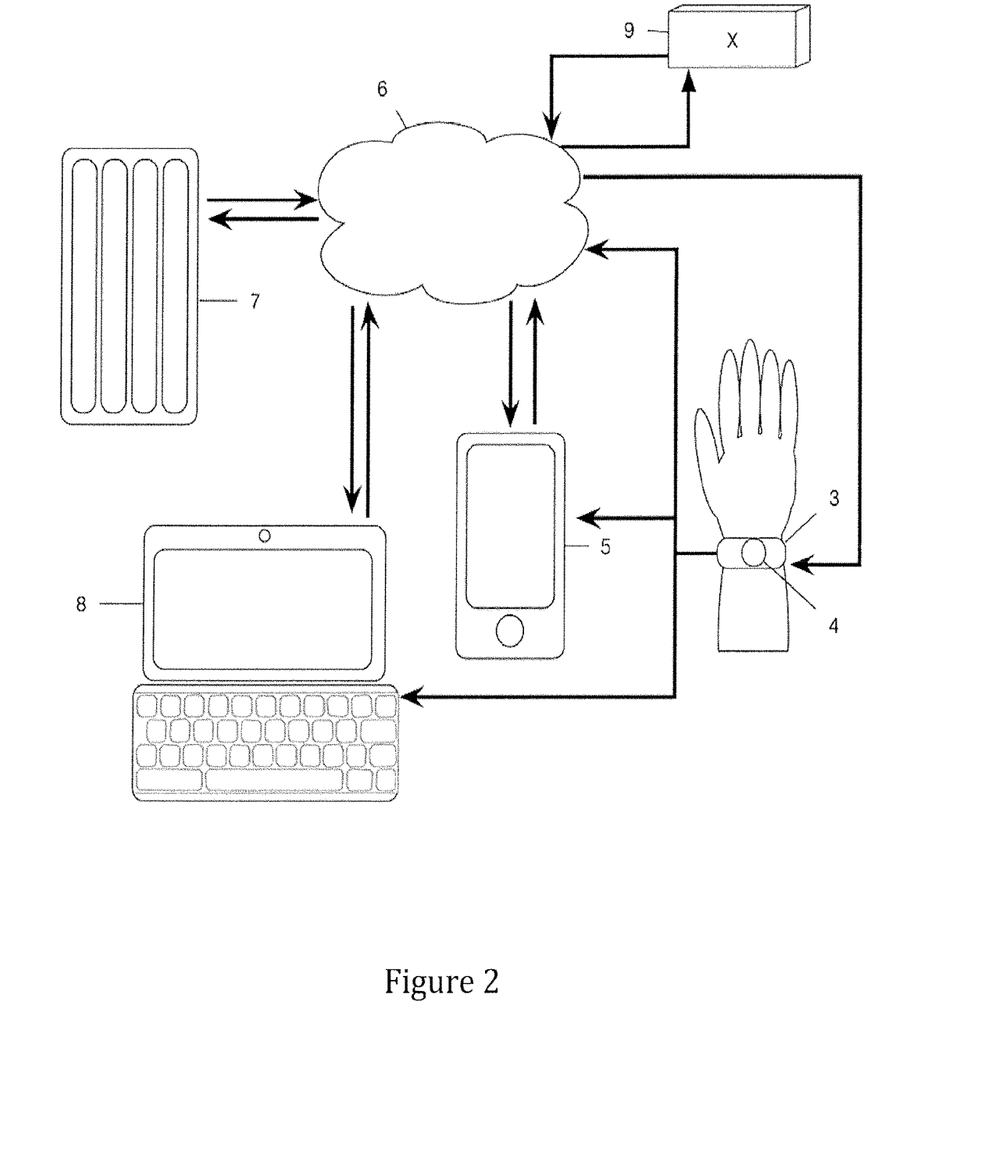
FIG. 2: A basic embodiment of the apparatus of the invention in the context of mobile and internet technologies.

FIG. 2 depicts a basic embodiment of the invention where 3 is the wearable PPG device containing the necessary sensor and processor means to measure an absorbance signal and determine heart rate. The wearable device optionally contains a display (4) and is capable of transmitting data to a mobile device (5) and or directly to an internet based platform (6). The data can be stored and further processed on a server (7) for future retrieval and to be viewed on a computing platform exemplified by the personal computer (8), the mobile phone (5) and or wearable device (3). It should be appreciated that the EPOC and estimated blood lactate levels determined using the current invention can be linked to a biomathematical model (9) of human physiology (in a preferred embodiment this biomathematical model is cloud based but can also be run on a local processor) to access hormonal changes, body composition changes or other physiological fluctuations or transient physiological behavior. The above-mentioned biological models can be coupled to the supply-demand differential equation that is used to determine EPOC. In an embodiment of the current invention, PPG and accelerometer signals are input into a biomathematical model linked to the demand block of the supply-demand EPOC equation and this can provide additional information about the exact physiological load/work intensity or real-time $VO_2$ demand of the subject. Incorporated herein in its entirety is the provisional patent application 62/068,882 which describes how real-time physiological load is determined from PPG and accelerometer data. This method assumes a mapping between measured activity and physiological energy demand. It is able to predict what the steady-state oxygen consumption is given a measure of activity level in conjunction with heart rate data. Similarly in another embodiment of the current invention, where one keeps in mind that EPOC is determined by integrating over time the difference between the supposed steady state oxygen consumption rate for a given physiological state (nearly always considered as rest after an exercise session in the literature) and the measured or inferred time varying oxygen consumption rate, it is possible to include biomathematical models to augment our estimate of either said steady state rate or said time varying rate to improve the accuracy of the EPOC calculation. Here the provisional patent application 62/068,882 is again a good example, showing how the steady state oxygen consumption rate can be estimated using easily accessible physiological signals.

Figure 3:
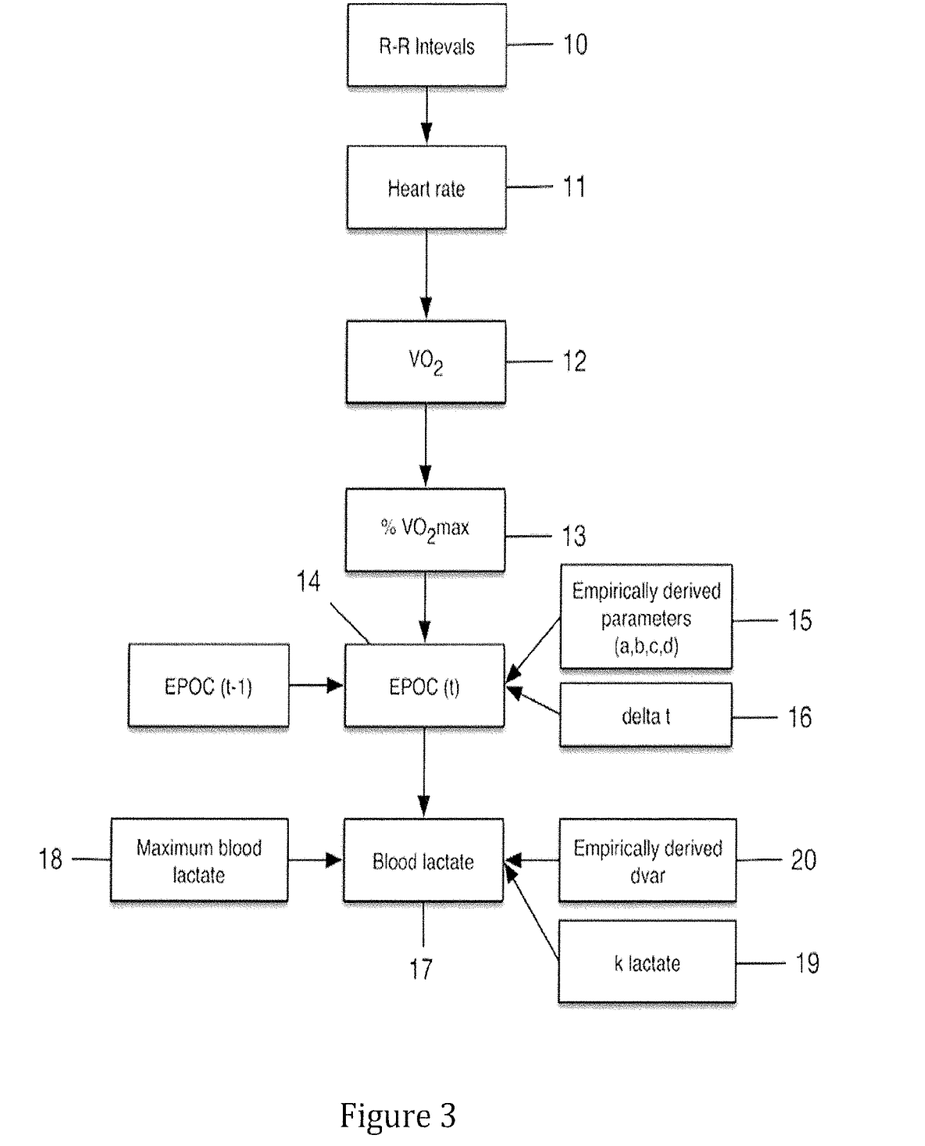
FIG. 3: A schematic representation of the overall method of the current invention illustrated by a flow diagram.

FIG. 3 depicts a flow diagram of an exemplary embodiment of the current invention. In the first step, the heart rate is determined (10), using the measured R-R intervals, frequency domain technique such as Fourier spectrum analysis or other means, and the relationship between the $HR_{reserve}$ ($HR_{max}$-$HR_{rest}$) and $VO_{2reserve}$ ($VO_{2max}$-$VO_{2rest}$) is computed. From this relationship, it is possible to determine the current oxygen consumption ($VO_2$) (11) and therefore the Percentage $VO_{2max}$ (12) that the subject is currently performing at.

The change in EPOC over time (13) is determined by a supply in reactions that increases EPOC and a demand in reactions that decreases EPOC. These reactions are conveniently incorporated into a supply ($f_{supply}$) and demand ($f_{demand}$) reaction block (equation 1). Percentage $VO_{2max}$ (V), whether directly measured or inferred from heart rate, is used to parameterize the supply block ($f_{supply}$) and V is also used, along with EPOC, to parameterize the demand block ($f_{demand}$). A non-abstracted version of equation 1 is presented in equation 2 where $f_{supply}=a*e^{b*V}$ and $f_{demand}=EPOC*c*e^{d*(1-V)}$. From the $f_{supply}$ equation it is evident that, as V increases the $f_{supply}$ reaction also increases. The parameters a and b (14) in the $f_{supply}$ equation are empirically determined and e is the base of the natural logarithm. Also, from the $f_{demand}$ equation it is evident that, as V increases the $f_{demand}$ reaction decreases. In addition, the EPOC term in the $f_{demand}$ equation simply indicates that, as EPOC increases, the $f_{demand}$ reaction increases causing the change of EPOC (equation 2) to slow down. The parameters c and d (14) in the $f_{demand}$ equation are empirically determined and e is the base of the natural logarithm. Equation 2, including both the $f_{supply}$ and $f_{demand}$ blocks, ensures that as an individual trains at a higher V the positive rate of change in EPOC also increases until a point of saturation is achieved. V can also denote percentage $VO_{2reserve}$ instead of percentage $VO_2$max, but then the parameters a, b, c and d will be different when determined empirically.

$$\frac{dEPOC}{dt} = f_{supply}(V) - f_{demand}(V, EPOC) \tag{1}$$

$$\frac{dEPOC}{dt} = a*e^{b*V} - c*e^{d*(1-V)}*EPOC \tag{2}$$

Practically, EPOC is initialized at zero (equation 3). Subsequently EPOC at time t+1 is determined by adding the $f_{supply}-f_{demand}$ value to EPOC at time t (15) (equation 4). Equation 5 shows a non-abstracted version of equation 4. The parameters a, b, c and d are the same as previously described.

$$EPOC=0 \tag{3}$$

$$EPOC_{(t+1)}=EPOC(t)+f_{supply}-f_{demand} \tag{4}$$

$$EPOC_{(t+1)}=EPOC(t)+a*e^{b*V}-c*e^{d*(1-V)}*EPOC(t) \tag{5}$$

Even though there is no clear causal association between lactate metabolism and elevated oxygen uptake, post-exercise oxygen can be used to estimate blood lactate (16). $lactate_{max}$ (17) is the maximal blood lactate achievable (approximately 25 mmol/l). klactate (18) is empirically derived and dvar (19) is a parameter that ensures that, at EPOC=0, blood lactate is initialized at a non zero value (resting blood lactate value).

$$\text{Estimated blood lactate} = \frac{lactate_{max}*(dvar+EPOC)}{klactate+EPOC} \tag{6}$$

Figure 4:
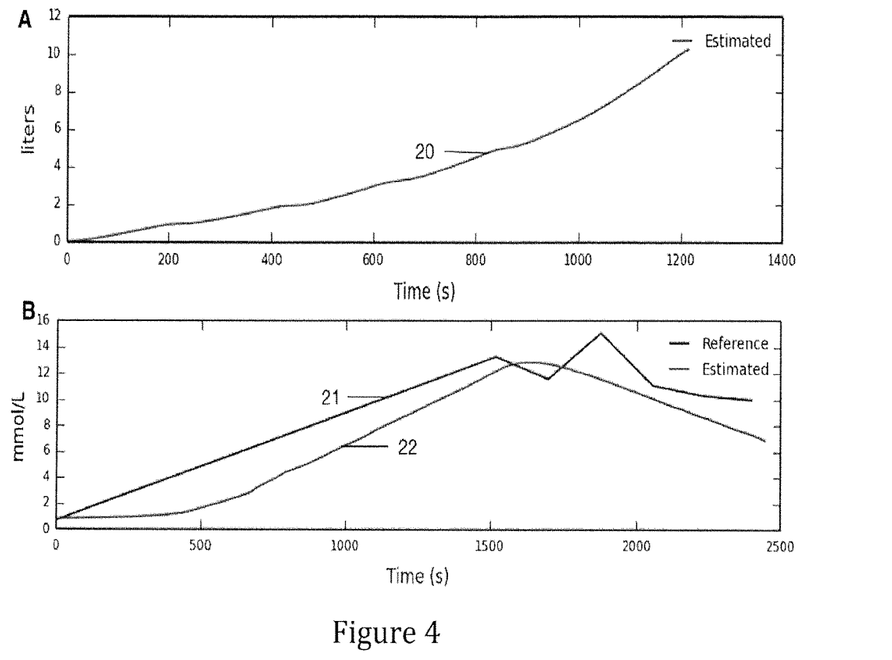
FIG. 4: (A) EPOC and (B) estimated blood lactate determined using the method of the current invention. Estimated blood lactate is compared to measured blood lactate levels.

FIG. 4A depicts an exemplary embodiment of a plot of EPOC (L) (20) over time (seconds) generated using heart rate data from a wearable PPG sensor and the method of the current invention. The data was collected from a subject who was performing a $VO_{2max}$ test and therefore the EPOC value rises to approximately 10 L after 20 minutes (1200 seconds).

FIG. 4B depicts an exemplary embodiment of a plot comparing measured (21) and estimated (22) blood lactate over time using the method of the current invention. Blood lactate is measured in mmol/L.

What is claimed:

1. A method for determining excess post-exercise oxygen consumption (EPOC) and an estimated blood lactate level of an individual, the method comprising:
    (a) capturing PPG light absorbance data from at least one optical sensor in contact with skin of the individual, wherein the at least one optical sensor is within a wearable device;
    (b) transforming the PPG light absorbance data, via a processor of the wearable device, into raw physiological signals of the individual;

(c) determining, via the processor, physiological parameters of the individual from the raw physiological signals, including:
  i. a continuous heart rate (HR), determined HR, $HR_{max}$, and $HR_{rest}$;
  ii. $HR_{reserve}$ which is the difference between the individual's $HR_{max}$ and $HR_{rest}$;
  iii. oxygen consumption ($VO_2$), $VO_{2max}$ and $VO_{2rest}$;
  iv. $VO_{2reserve}$ which is the difference between the individual's $VO_{2max}$ and $VO_{2rest}$; and
  v. exercise intensity;
(d) applying a supply-demand differential equation to at least one of the determined physiological parameters to determine the EPOC;
(e) calculating the estimated blood lactate level as a function of the EPOC;
(f) transmitting the determined EPOC and the estimated blood lactate level to a mobile computing device, a cloud-based platform, or a personal computer; and
(g) incorporating a biomathematical model of human physiology to calculate additional parameters from the determined EPOC and the estimated blood lactate level, wherein the biomathematical model comprises biomathematical models of metabolism, body composition change, hormonal changes or any other biomathematical model that describes a physiological process.

2. The method of claim 1, wherein the percentage $VO_{2max}$ and the exercise intensity are calculated as a function of the relationship between the $HR_{reserve}$ and the $VO_{2reserve}$.

3. The method of claim 1, wherein the determined EPOC is determined by the following supply-demand differential equation, where a supply in reactions increases EPOC ($f_{supply}$), and a demand in reactions decreases EPOC ($f_{demand}$):

$$EPOC_{(t+1)} = EPOC(t) + a*e^{b*v} - c*e^{d*(1-v)}*EPOC(t),$$

wherein
V is the Percentage $VO_{2max}$,
EPOC=0(initialized),
$a*e^{b*v}$ is the $f_{supply}$,
$c*e^{d*(1-V)}$ is the $f_{demand}$,
a, b, c and d are empirically determined parameters,
e is the base of the natural logarithm, and
t is time.

4. The method of claim 1, wherein the estimated blood lactate level is calculated as a function of the determined EPOC by applying the following equation:

$$\text{Estimated blood lactate level} = \text{lactate}_{max}*(\text{dvar}+\text{EPOC}), \text{klactate}+\text{EPOC}$$

wherein
$\text{lactate}_{max}$ is the maximal blood lactate achievable (approximately 25 mmol/L),
klactate is an empirically derived parameter, and
dvar is a parameter that ensures that, at EPOC=0, blood lactate is initialized at a non-zero value.

5. The method of claim 1, wherein the biomathematical model is a cloud-based biomathematical model.

6. The method of claim 1, wherein transmitting the determine EPOC and the estimated blood lactate level further comprises transmitting at least one of the following: the continuous HR data, the determined HR, the raw physiological signals, and the determined physiological parameters.

7. The method of claim 6, wherein at least one of the continuous HR data, the determined HR, the determined EPOC, the raw physiological signals, the determined physiological signals and the estimated blood lactate level is transmitted wirelessly to a platform to be stored, analyzed and viewed on client computing platforms, including a mobile computing device, a personal computer and a wearable electronic device.

8. The method of claim 1, further comprising acquiring accelerometer signals, wherein at least one of the physiological parameters is incorporated with data from the accelerometer signal to further generate the determined physiological parameters.

9. A system for determining excess post-exercise oxygen consumption (EPOC) and an estimated blood lactate level of an individual from a photoplethysmography (PPG) signal, the system comprising a server and a wearable device, the wearable device comprising:
at least one optical sensor that collects PPG light absorbance data from the individual when in contact with skin of the individual;
and a processor, the processor configured to:
  (a) acquire the PPG light absorbance data from the at least one optical sensor;
  (b) determine the individual's heart rate (HR) data, including determined HR, continuous HR, $HR_{max}$, and $HR_{rest}$ from the PPG light absorbance data via the processor of the wearable device;
  (c) determine additional physiological parameters of the individual from the PPG light absorbance data including $HR_{reserve}$ which is the difference between the individual's $HR_{max}$, $HR_{rest}$, oxygen consumption ($VO_2$), $VO2_{max}$, $VO2_{rest}$ and $VO2_{reserve}$ which is the difference between the individual's $VO2_{max}$ and $VO2_{rest}$;
  (d) calculate the individual's exercise intensity from the PPG light absorbance data, the HR, $HR_{max}$, $HR_{rest}$, or the additional physiological parameters;
  (e) apply a supply-demand differential equation to at least one of the physiological parameters to determine EPOC;
  (f) calculate the estimated blood lactate level as a function of the determined EPOC; and
  (g) transmit the determined EPOC and the estimated blood lactate level to the server, wherein the server is configured to incorporate a biomathematical model of human physiology to calculate additional parameters from the determined EPOC and the estimated blood lactate level, wherein the biomathematical model comprises biomathematical models of metabolism, body composition change, hormonal changes or any other biomathematical model that describes a physiological process.

10. The system of claim 9, wherein the percentage $VO_{2max}$ and exercise intensity are calculated as a function of the relationship between $HR_{reserve}$ and $VO_{2reserve}$.

11. The system of claim 9, wherein the determined EPOC is determined by the following supply-demand differential equation, where a supply in reactions increases EPOC ($f_{supply}$), and a demand in reactions decreases EPOC ($f_{demand}$):

$$EPOC_{(t+i)} = EPOC(t) + a*e^{b*V} - c*e^{d*(1-V)}*EPOC(t),$$

wherein
V is the Percentage $VO_{2max}$,
EPOC=0(initialized),
$a*e^{b*V}$ is the $f_{supply}$,
$c*e^{d*(1-V)}$ is the $f_{demand}$,
a, b, c and d are empirically determined parameters, e is the base of the natural logarithm, and t is time.

12. The system of claim 9, wherein the blood lactate level is calculated as a function of the determined EPOC by applying the following equation:

$$\text{Estimated blood lactate level} = \text{lactate}_{max} * (d_{var} + EPOC) \text{klactate} + EPOC$$

wherein $\text{lactate}_{max}$ is the maximal blood lactate achievable (approximately 25 mmol/L), klactate is an empirically derived parameter, dvar is a parameter that ensures that, at EPOC=0, and blood lactate is initialized at a non-zero value.

13. The system of claim 9, wherein the biomathematical model is a cloud-based biomathematical model that runs on the processor of the wearable device.

14. The system of claim 9, wherein the processor is further configured to transmit at least one of the continuous HR, the determined HR, the raw physiological signals, and the determined physiological signals.

15. The system of claim 14, wherein at least one of the continuous HR, the determined HR, the determined EPOC, the raw physiological signals, the determined physiological parameters and the estimated blood lactate level is transmitted wirelessly to a platform where it is stored, analyzed and viewed on at least one of the following client computing devices: a mobile computing device, a personal computer and a wearable electronic device.

16. A wearable device for determining excess post-exercise oxygen consumption (EPOC) and an estimated blood lactate level of an individual comprising:
   (a) at least one optical sensor in contact with the individual's skin, wherein the optical sensor is configured to capture PPG light absorbance data when in contact with the individual's skin; and
   (b) a processor, wherein the processor is configured to:
      (i) generate raw physiological signals from the PPG light absorbance data;
      (ii) determine the individual's heart rate from the raw physiological signals
      (iii) determine physiological parameters from the heart rate and the raw physiological signals, including $HR_{reserve}$ which is the difference between the individual's $HR_{max}$ and $HR_{rest}$, and
      oxygen consumption ($VO_2$) reserve, which is the difference between the individual's $VO_{2max}$ and $VO_{2rest}$,
      (iv) calculate the individual's percentage $VO_{2max}$ and exercise intensity,
      (v) apply a supply-demand differential equation to at least one of the physiological parameters to determine EPOC from the determined heart rate and calculate the estimated blood lactate level of the individual as a function of EPOC, and
      (vi) incorporate a biomathematical model of human physiology to calculate additional parameters from the determined EPOC and the determined heart rate, wherein the biomathematical model comprises biomathematical models of metabolism, body composition change, hormonal changes or any other biomathematical model that describes a physiological process.

17. The device of claim 16, wherein the wearable device is further configured to obtain accelerometer data for the individual and the processor incorporates the accelerometer data with the PPG light absorbance data to generate the biomathematical model.

18. The device of claim 16, wherein at least one of the PPG light absorbance data, the determined physiological parameters, the determined heart rate, the determined EPOC and the estimated blood lactate level is transmitted to at least one of the following client computing devices where it can be stored, analyzed and viewed: a mobile computing device and a personal computer.

* * * * *